United States Patent [19]
Bachmann et al.

[11] Patent Number: 5,347,226
[45] Date of Patent: Sep. 13, 1994

[54] ARRAY SPREADING RESISTANCE PROBE (ASRP) METHOD FOR PROFILE EXTRACTION FROM SEMICONDUCTOR CHIPS OF CELLULAR CONSTRUCTION

[75] Inventors: Walter A. Bachmann, Sunnyvale; Peggy A. Hale, Ben Lomond, both of Calif.

[73] Assignee: National Semiconductor Corporation, Santa Clara, Calif.

[21] Appl. No.: 977,264

[22] Filed: Nov. 16, 1992

[51] Int. Cl.$^5$ ............................................ G01R 27/02
[52] U.S. Cl. ................................ 324/724; 324/719; 324/722; 437/8; 29/592.1
[58] Field of Search ............... 324/719, 722, 724, 537; 437/8, 228; 29/592.1

[56] References Cited

U.S. PATENT DOCUMENTS

| | | | |
|---|---|---|---|
| 3,287,637 | 11/1966 | Keller | 324/719 X |
| 4,163,243 | 7/1979 | Kamins et al. | |
| 4,267,506 | 5/1981 | Shiell | 324/158 P |
| 4,290,186 | 9/1981 | Klein et al. | |
| 4,413,401 | 11/1983 | Klein et al. | |
| 4,888,546 | 12/1989 | Berry et al. | 324/722 X |
| 5,023,561 | 6/1991 | Hillard | 324/719 |

OTHER PUBLICATIONS

C. Sodini et al.; Enhanced Capacitor for One-Transistor Memory Cell; IEEE Trans.; Electron Devices; ED-23, 1187 (1976) (no month).
How Big a Pattern Do We Need for Spreading Resistance Analysis?; Solecon Labs Technical Note, Jun. 7, 1990.
D. K. Schroder; Semiconductor Material and Device Characterization; Wiley, New York, (1990); (no month).
Standard test Method for Measuring Resistivity Profiles Perpendicular to the Surface of a Silicon Wafer Using a Spreading Resistance Probe; 1988 Annual Book of ASTM Standards, American Soc. of Test. Mater. Conf., Philadelphia, (1988) (no month).
R. Brennan et al.; Determination of Diffusion Characteristics Using Two-and Four-Point Probe Measurements; Solid-State Technology, 27, 125, (1984) (no month).
R. J. Hilliard et al.; Profiling of Silicon and III-V Compounds by Point Contact Technologies; Solid-State Technology; 32, 119 (1989) (no month).
J. R. Ehrstein; Spreading Resistance Measurements-An Overview; Emerging Semiconductor Technology, ASTm STP 960; American Soc. Test. Mater. Conf. Philadelphia (1986) (no month).
S. C. Choo et al.; Extraction of Semiconductor Dopant Profiles from Spreading Resistance Data: An Inverse Problem; Solid-State Electronics, 33, 783 (1990) (no month).
R. G. Mazur et al.; "A Spreading Resistance Technique for Resistivity Measurements on Silicon"; J. Electrochem Society, 113, 255 (1966) (no month).
PSI Probe; Park Scientific Instruments; Spring 1992; Technical Newsletter (no month).
Wayne B. Grabowski; Simulation of SRP Bevel Effects; Application Note 1001; Tech. Modeling Associates, Inc.; pp. 1-4; 1986.

(List continued on next page.)

Primary Examiner—Kenneth A. Wieder
Assistant Examiner—Glenn W. Brown
Attorney, Agent, or Firm—Limbach & Limbach

[57] ABSTRACT

A semiconductor scanning resistance probe which has a support structure formed on a top surface of a substrate to form a cantilever. The support structure has a plurality of openings which extend through the support structure from a connector end to a cone end. An outer surface of the support structure at one side of each opening is cone-shaped so that an apex of the cone forms the cone end. A probe tip is formed in each probe tip opening and along the surface of the support structure. The probe tips are placed on individual semiconductor devices to extract impurity profiles.

33 Claims, 18 Drawing Sheets

OTHER PUBLICATIONS

Three Dimensional Measurement of Submicron Patterns; High-Tech Report; Jun. 1987, pp. 85-86, JEE.

Yasutake et al.; Scanning tunneling microscope combined with optical microscope for large sample measurement; J. Vac. Sci. Technology A 8 (1) Jan./Feb. 1990; pp. 350-353.

Hansma et al.; Scanning Tulleling Microscopy and Atomic Force Microscopy: Application to Biology and Technology; Articles; Oct. 14, 1988; pp. 209-216; Science vol. 242.

N. Barniol, et al.; Simple STM Theory; Vacuum; vol. 41, Nos. 1-3; pp. 379-381; 1990 (no month).

Gabi Neubauer et al.; Imaging VLSI Cross Sections by Atomic Force Microscopy; Intel Corp. IEEE/IRPS, 1992, pp. 299-303 (no month).

Richard Chapman et al.; Model and Simulation of Scanning Tunneling Microscope tip/Semiconductor Interactions in PN Junction Delineation; 1992 American Vacuum Society; vol., 10, No. 1, Jan.Feb. 1992.

Yi Chiu, et al.; Doping Profiles Studied by Scanning Tunneling Spectroscopy; Jan. 27, 1992.

ARRAY SPREADING RESISTANCE PROBE (ASRP) METHOD FOR PROFILE EXTRACTION FROM SEMICONDUCTOR CHIPS OF CELLULAR CONSTRUCTION

BACKGROUND OF THE INVENTION

1. Field of the Invention

The present invention relates to probing and analysis of semiconductor integrated circuits and in particular, to a probe for extracting dopant profiles from semiconductor structures.

2. Description of the Related Art

The most commonly used method for the generation of resistivity or carrier concentration profiles perpendicular to the surface of a processed semiconductor wafer is the Spreading Resistance Probe (SRP) method. See R. G. Mazur and D. H. Dickey, "A Spreading Resistance Technique for Resistivity Measurements in Si", *J. Electrochem. Soc.*, 113, 255 (1966).

The conventional SRP method is described in various reference works. See for example: D. K. Schroder, *Semiconductor Material and Device Characterization*, Wiley, New York (1990); ASTM Standard F672 "Standard Method for Measuring Resistivity Profile Perpendicular the Surface of a Silicon Wafer Using a Spreading Resistance Probe", 1988 *Annual Book of ASTM Standards*, American Soc. of Test. Mater. Conf., Philadelphia (1988); R. Brennan and D. Dickey, "Determination of Diffusion Characteristics Using Two-and Four-Point Probe Measurements, Solid-State Technology, 27, 125 (1984); and R. J. Hillard, R. G. Mazur, H. L. Berkovits, and P. Rai-Choudhury, "Profiling of Silicon and III–IV Compounds by Point-Contact Techniques", *Solid-State Technology*, 32, 119 (1989).

As shown generally in FIG. 1, and in greater detail in FIG. 2, the conventional SRP method uses a two-point resistance measurement on a bevelled surface. The total resistance $R_T$ measured between the probes has several components, i e., $$R_T = 2R_c + 2R_{sp} + R_s \sim 2R_{sp}, \qquad (1)$$

where $R_c$ is the contact resistance, $R_{sp}$ is the spreading resistance and $R_s$ is the semiconductor resistance between the probe contacts. The spreading resistance $R_{sp}$ accounts for the resistance encountered by the current I when it flows from the metal probe into the semiconductor material.

For analytical purposes, the probe can be approximated as a highly conductive, cylindrical bar that is placed into non-indenting contact with a semi-infinite semiconductor block. It has been demonstrated (see Hillard et al., Ibid) that such an arrangement yields a spreading resistance $$R_{sp} = \rho/(4r), \qquad (2)$$

where $\rho$ is the semiconductor resistivity and $r$ is the probe radius.

It can easily be seen that if the probe radius r is made small enough and the contact resistance $R_c$ is minimized, then the spreading resistance $R_{sp}$ becomes the dominant component of the total resistance $R_T$, as reflected in Eq. (1). Moreover, about 80% of the potential drop due to the spreading phenomenon occurs within a distance of five times the contact radius, which makes the SRP method a good tool for local resistivity characterization.

The application of this method to actual resistivity measurements involves complex calculations, the result of which is a multiplicative correction factor to Eq (2). Furthermore, application of the method to non-uniform doping profiles involves mathematical and physical analysis making up a specialized literature that has been generated by a confined circle of authors. See, for example, J. R. Ehrstein, "Emerging Semiconductor Technology, *ASTM* STP 960 (Edited by D. C. Gupta and P. H. Langer), American Soc. Test. Mater. Conf. Philadelphia (1986); and S. C. Choo, M. S. Leong, C. B. Liem and K. C. Kong, "Extraction of Semiconductor Dopant Profiles from Spreading Resistance Data: An Inverse Problem", *Solid-State Electronics*, 33, 783, (1990).

Most recently, space-charge effects have been observed to influence SRP measurements (specifically in deep profiles). These effects are accounted for utilizing advanced simulation tools. See W. B. Grabowski, "Simulation of SRP Bevel Effects", Application Note 1001, Technology Modeling Associates, Inc., Palo Alto (1986).

Although the SRP method is the most commonly used procedure for measuring processed semiconductor wafers, it is frequently desireable to measure actual semiconductor devices rather than a processed semiconductor wafer. The Mazur/Dickey SRP method requires the wafer to have specially devised rectangular patterns of 1,000 μm × 100 μm (preferred dimensions), or at least 200 μm × 40 μm. See "How Big a Pattern Do We Need for Spread Resistance Analysis", Solecon Labs Technical Note, Jun. 7, 1990.

Since most semiconductor devices are substantially smaller than the minimum sizes required by the Mazur/Dickey SRP method, the Mazur/Dickey SRP method cannot be used to measure an actual semiconductor device except where the largest semiconductor devices are involved.

Additionally, the physical size of the SRP probes, which are typically several micrometers in diameter, are physically so large that it is impossible to profile very shallow junctions due to the mechanical punch through of the probes. Further, the conventional SRP technique only measures the junction depth and not the junction width.

Other techniques for extracting dopant profile are also available. The closest to satisfying the small-area requirements is the Secondary-Ion Mass Spectroscopy (SIMS) technique. See S. M. Sze, *VLSI Technology*, McGraw-Hill, New York, 1988. Although, theoretically, the ion-beam spot could be confined to a few micrometers in diameter, the SIMS method appears to be impractical and cost-inefficient under normal conditions. Moreover, the presence of the same doping element, i.e., boron, in the field regions (under the field oxide) poses serious discrimination problems if the ion-beam spot intrudes into the respective regions.

It appears that no practical method is currently available for the extraction of impurity profiles from individual devices on a semiconductor wafer. Thus, there is a need for a device which can take profile measurements on individual devices.

DETAILED DESCRIPTION

Figure 1:
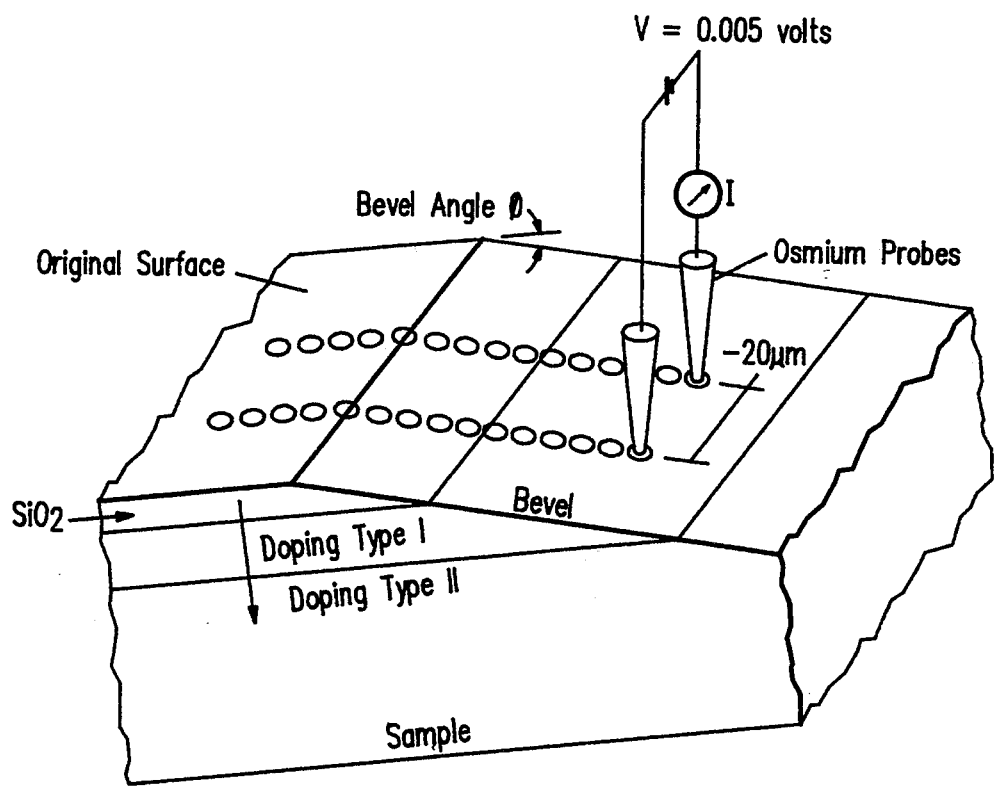
FIG. 1 provides an overall illustration of the conventional two-point SRP measurement on a bevelled surface.
Figure 2:
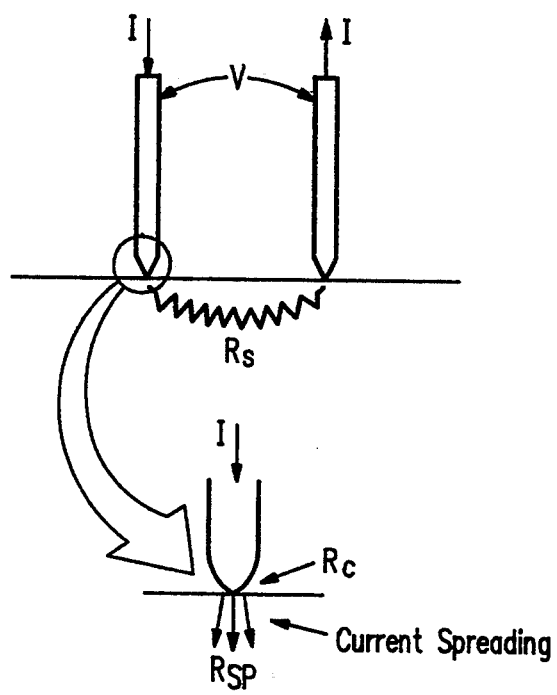
FIG. 2 provides a detailed illustration of the FIG. 1 measurement technique.
Figure 3:
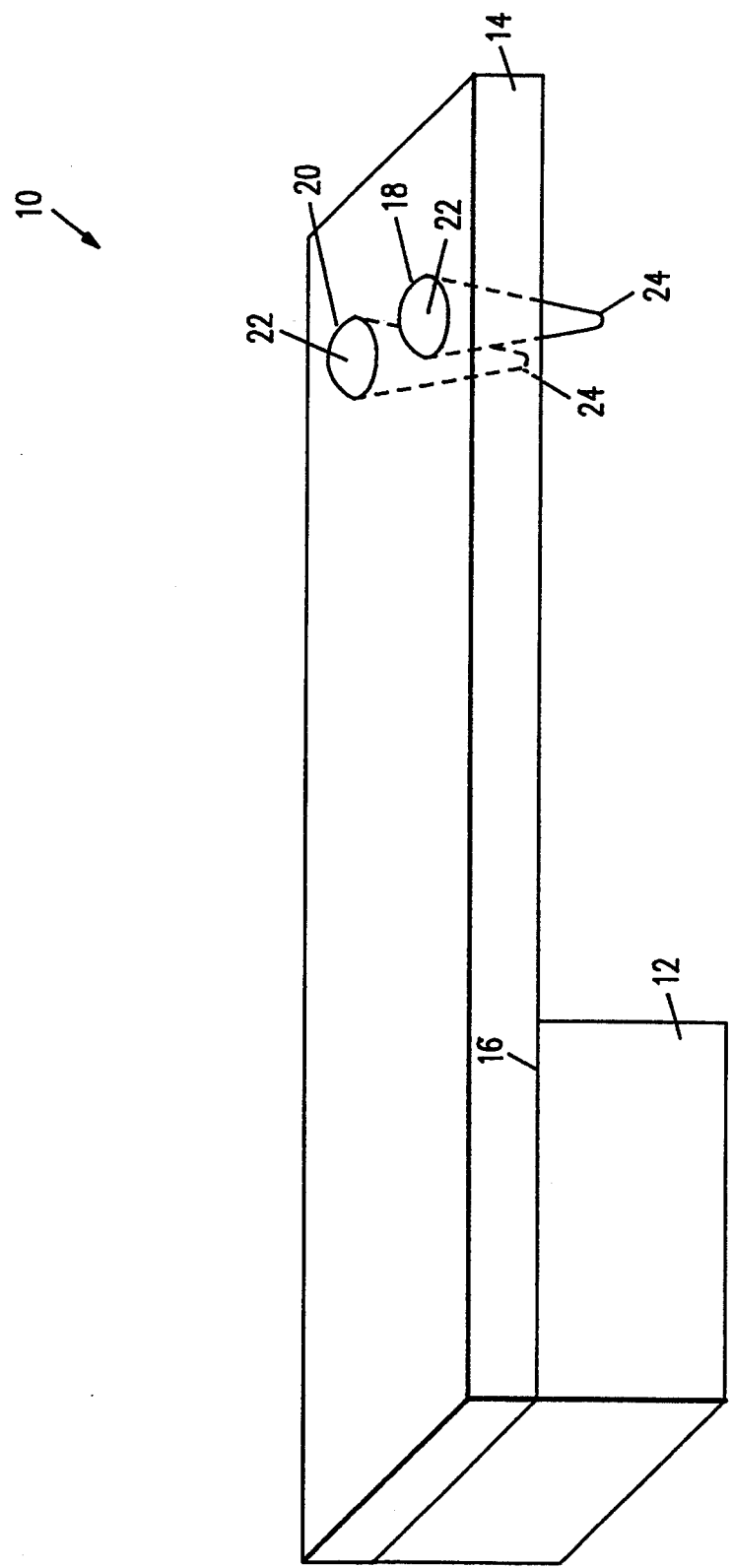
FIG. 3 is a top right-side perspective view illustrating a cantilever embodiment and two probe tips.

FIG. 3 shows semiconductor probe 10 in accordance with the present invention. Semiconductor probe 10 includes semiconductor substrate 12, support structure 14, which is formed on top surface 16 of semiconductor substrate 12 to form a cantilever, and two probe tips (not shown in FIG. 3) formed within support structure 12. As shown in FIG. 3, support structure 14 includes input probe tip opening 18 and output probe tip opening 20, each of which extend through support structure 14 from connector end 22 to cone end 24.

Figure 4:
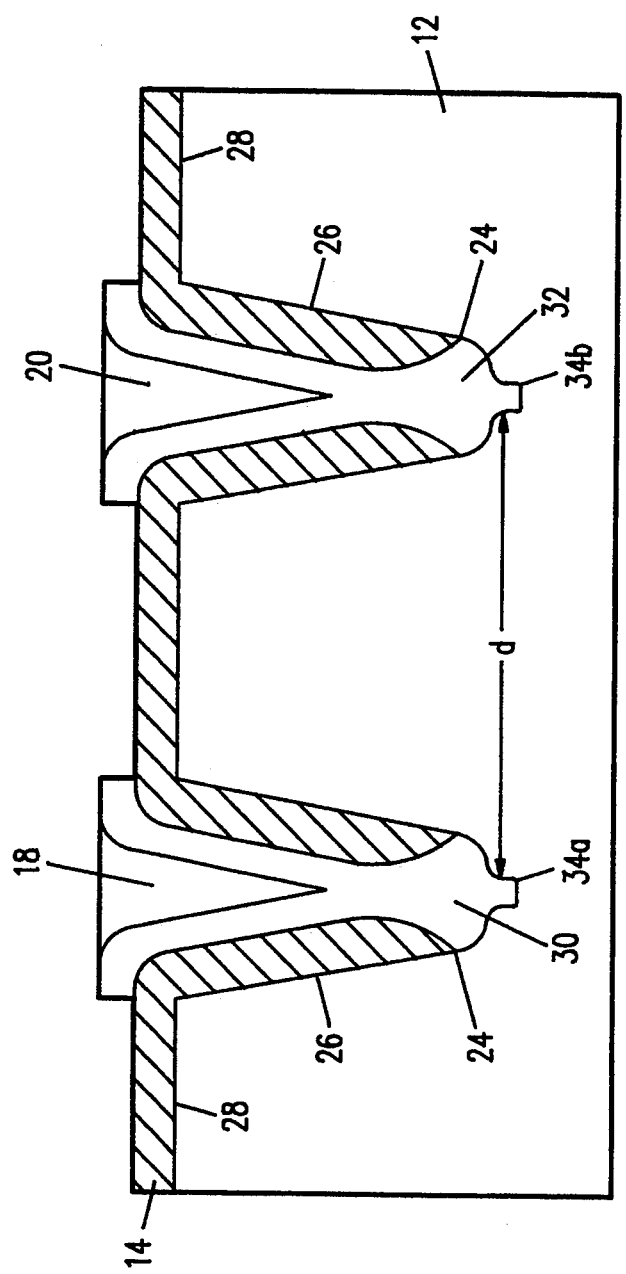
FIG. 4 is a distal end view illustrating the probe tips positioned within the support structure.

As shown in FIG. 4, outer surface 26 of support structure 14 is cone-shaped on lower side 28 of each probe tip opening 18 and 20 so that an apex of cone-shaped outer surface 26 forms cone end 24. Input probe tip 30 and output probe tip 32 are formed within input probe tip opening 18 and the output probe tip opening 20, respectively. Each probe tip 30 and 32 extends beyond cone end 24 of support structure 14 to form probe points 34a and 34b. Probe points 34a and 34b can be formed to have a sharp point, a ball point, or a cylindrical point.

Figure 5:
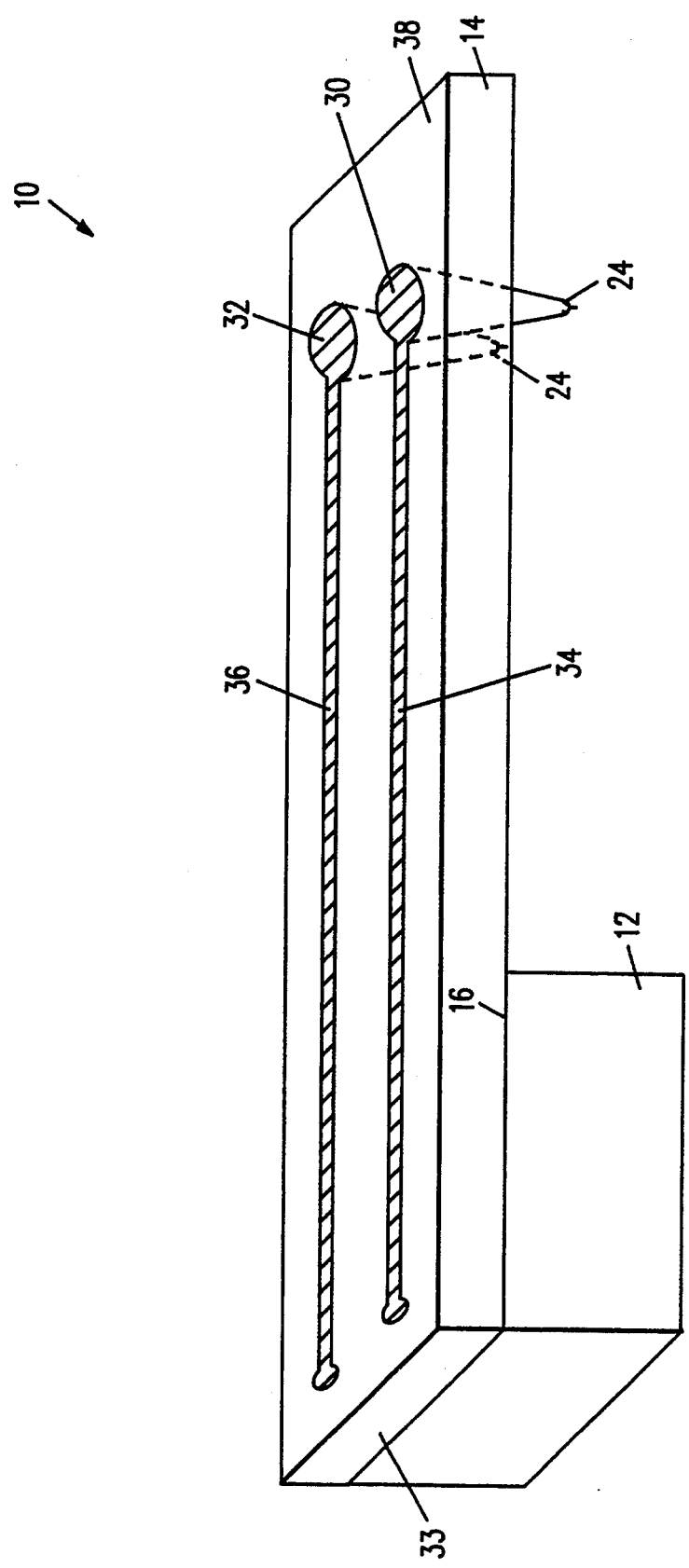
FIG. 5 is a top right-side perspective view illustrating the two probe tips and their associated conductors leading to the proximate end of the semiconductor probe.

Referring to FIG. 5, input probe tip 30 and output probe tip 32 are electrically connected to proximate end 33 of support structure 14 for connection to an external positioning and control device (not shown in FIG. 5) by input conductor 34 and output conductor 36, respectively, which are formed on top surface 38 of support structure 14. The external positioning and control device, which can be a scanning tunneling microscope, an atomic force microscope, or a similar device, has a positioning accuracy on the order of 0.1 microns.

Referring again to FIG. 4, in the present invention, the minimum probe separation distance d is approximately 1.0 microns. The miniumum probe separation distance d, however, is a function of the current state of the art in integrated circuit technology and not any limitation of the present invention. Thus, as integrated circuit technology produces smaller and smaller devices, the minimum separation distance d can also be reduced. Since the current minimum separation distance d is approximately 1.0 microns and since the external positioning and control device has a positioning accuracy on the order of 0.1 microns, semiconductor probe 10 can generate resistivity and carrier concentration profiles from an individual semiconductor device.

In operation, the external positioning and control device first places semiconductor probe 10 into physical contact with a semiconductor device. Once contact has been made, the external positioning and control device follows standard scanning resistance probe steps by providing a constant voltage differential, which is below the turn-on voltage of the semiconductor device, across input probe tip 30 and output probe tip 32, thereby generating a resistivity current for measurement.

When the external positioning and control device places input probe tip 30 and probe tip 32 into physical contact with the semiconductor device, approximately 30 Angstroms of oxides and approximately 30 Angstroms of hydrocarbons are frequently present on the surface of the semiconductor device as a result of exposure to the air. To enable input probe tip 30 and output probe tip 32 to break through the layers of oxides and hydrocarbons without punching through a potentially shallow junction below, a preferred embodiment of the semiconductor probe 10 further incorporates pressure sensing devices.

The pressure applied by external positioning and control device as semiconductor probe 10 is placed in physical contact with the semiconductor device can be measured with a strain gage and/or a mirror.

Figure 6:
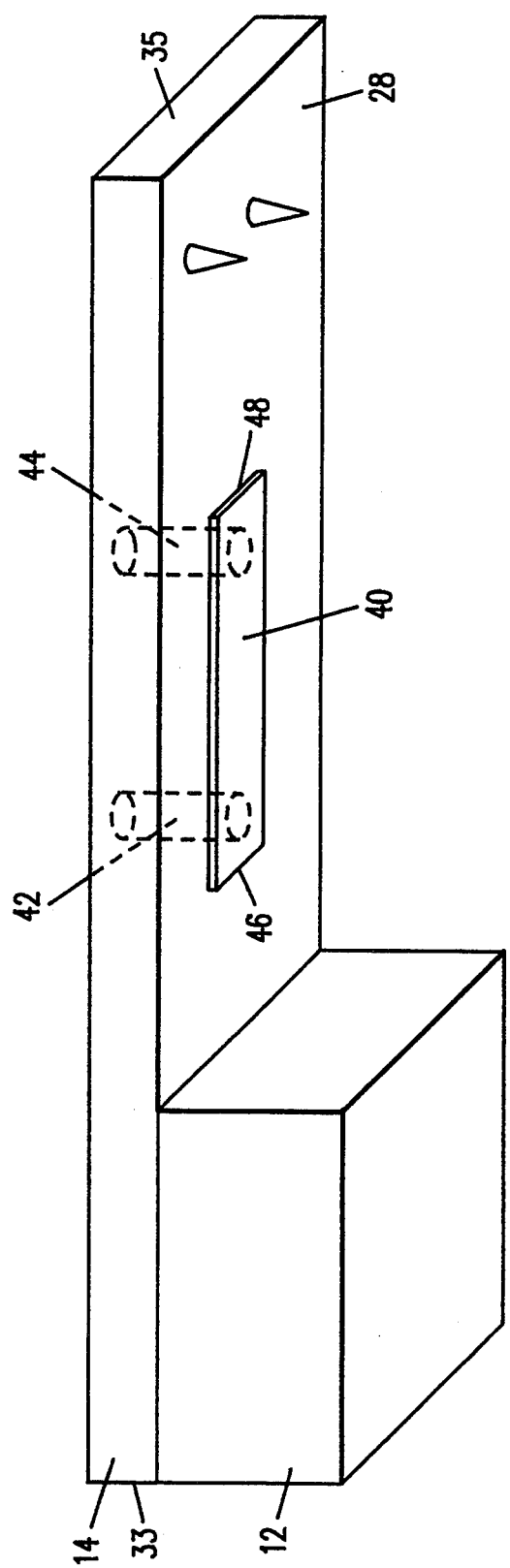
FIG. 6 is a bottom right-side perspective view illustrating the strain gage, the strain input and output openings, and the probe tips.

Referring to FIG. 6, strain gage 40 is formed on lower side 28 of support structure 14 at an intermediate position between proximate end 33 and distal end 35 of support structure 14. As shown in FIG. 6, strain input opening 42 and strain output opening 44 are formed within support structure 14 and extend through support structure 14 to expose input end 46 and output end 48 of strain gage 40.

Figure 7:
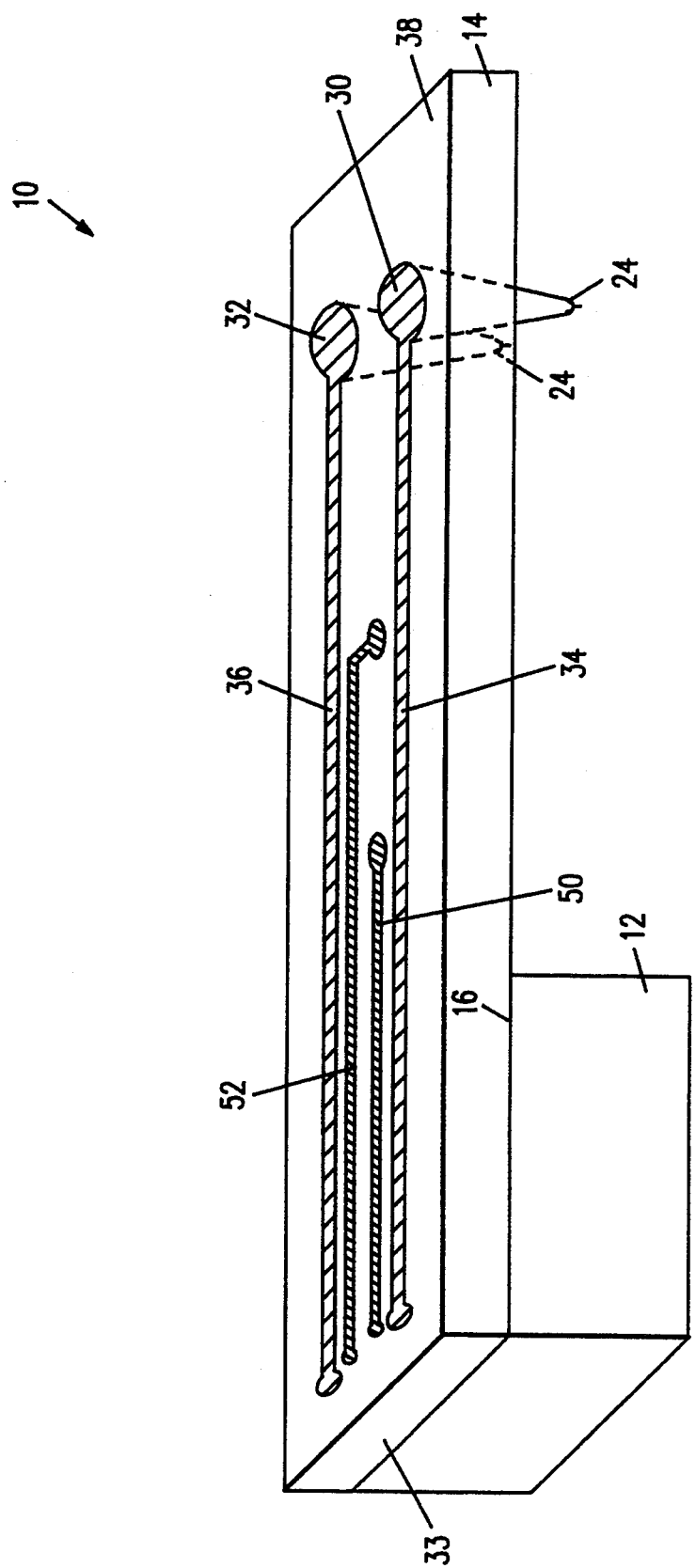
FIG. 7 is a top right-side perspective view illustrating the two probe tips and their associated conductors leading to the proximate end of the semiconductor probe and the strain input and output conductors leading to the proximate end.
Figure 8:
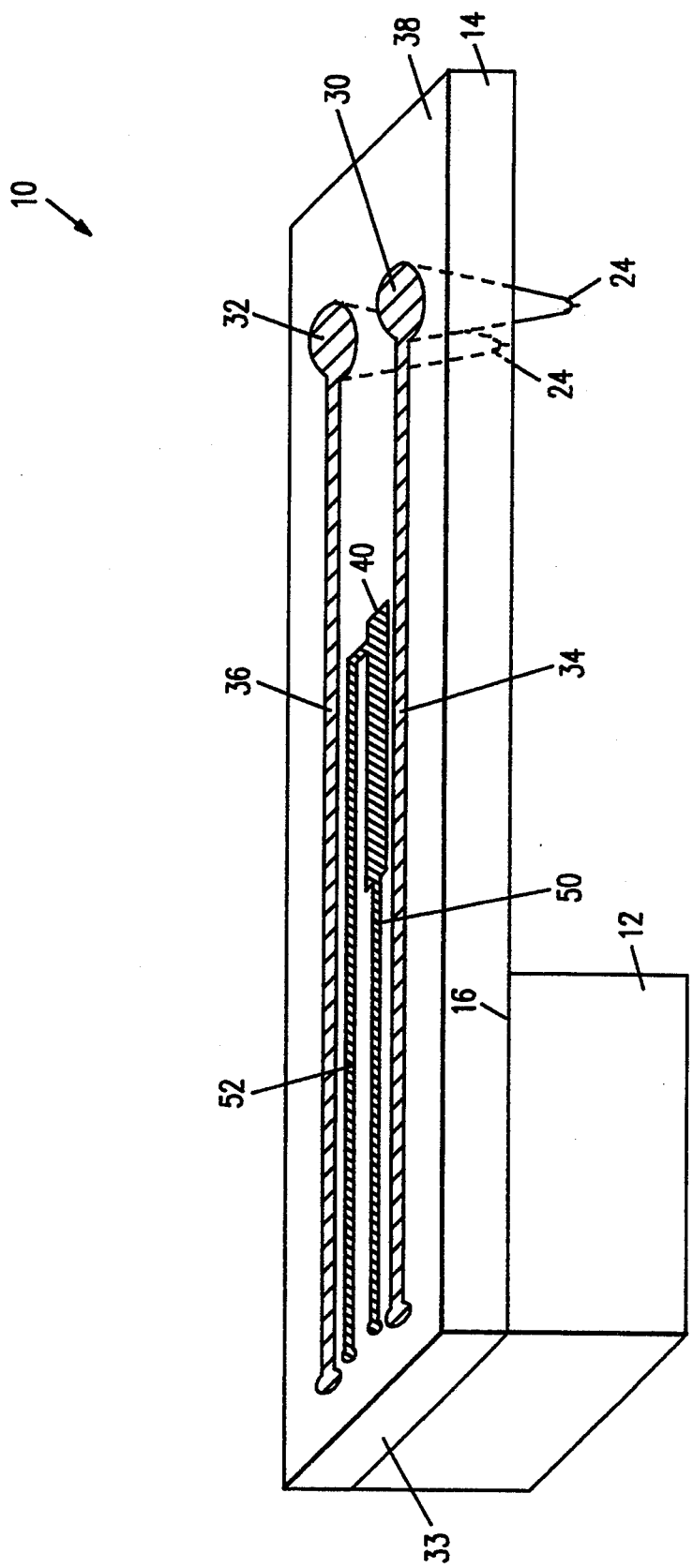
FIG. 8 is a top right-side perspective view illustrating the strain gage positioned on the top surface of the semiconductor probe.

As shown in FIG. 7, input end 46 and output end 48 of strain gage 40 are electrically connected to proximate end 33 of support structure 14 by strain input conductor 50 and strain output conductor 52, respectively. Strain input conductor 50 and strain output conductor 52 are formed on top surface 38 of support structure 14 and within strain input opening 42 and strain output opening 44, respectively. Alternatively, as shown in FIG. 8, strain gage 40 can be formed on top surface 38 of support structure 14.

Although not shown, it should be clear to one skilled in the art that strain gage 40 can be positioned at any location on support structure 14 that provides a sufficient deflection when the external positioning and control device presses semiconductor probe 10 onto a semiconductor device.

Strain gage 40 operates by providing a variable resistance which results from the deflection of support structure 14. By providing a constant current or a constant voltage source, the change in current or voltage due to the variable resistance can be calibrated to indicate the amount of deflection and thereby the amount of pressure exerted by the external positioning and control device.

Figure 9:
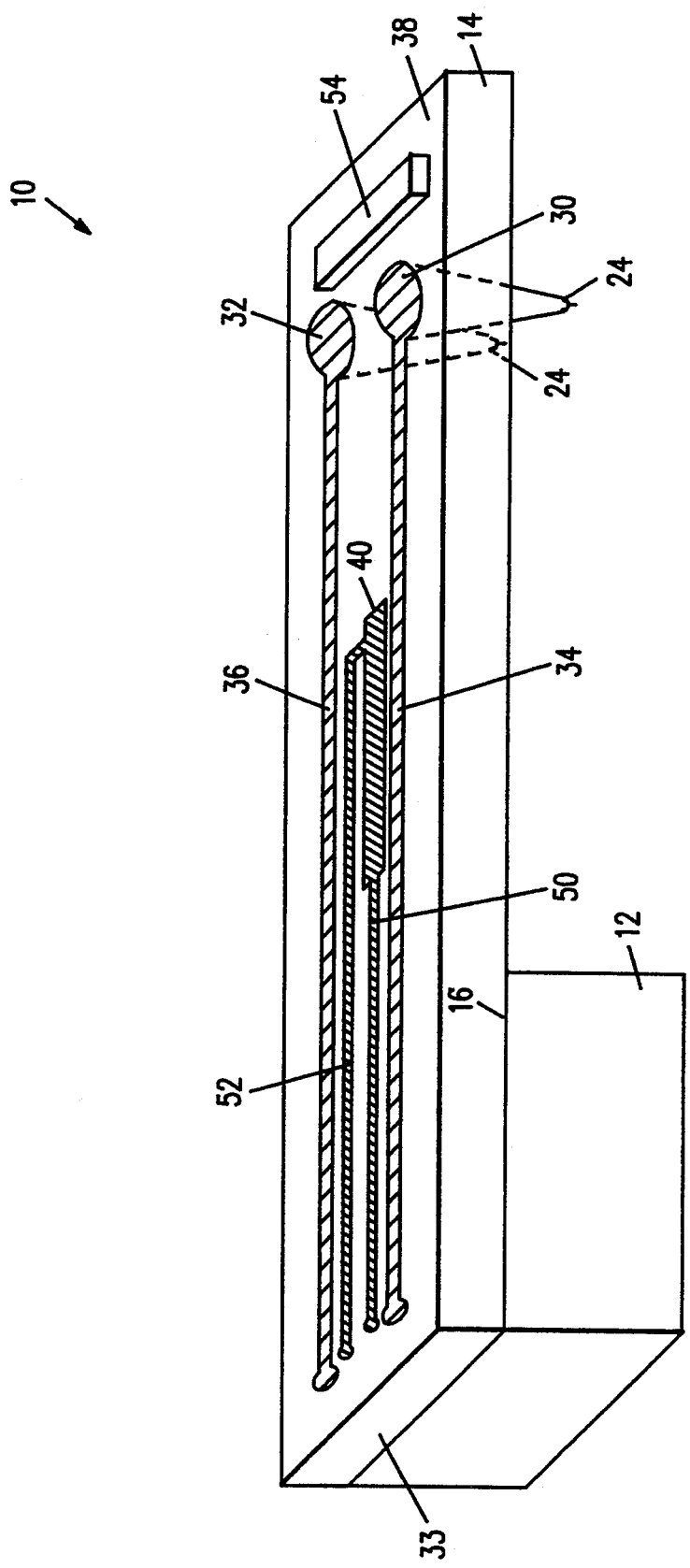
FIG. 9 is a top right-side perspective view illustrating the strain gage and the mirror positioned on the top surface of the semiconductor probe.
Figure 10:
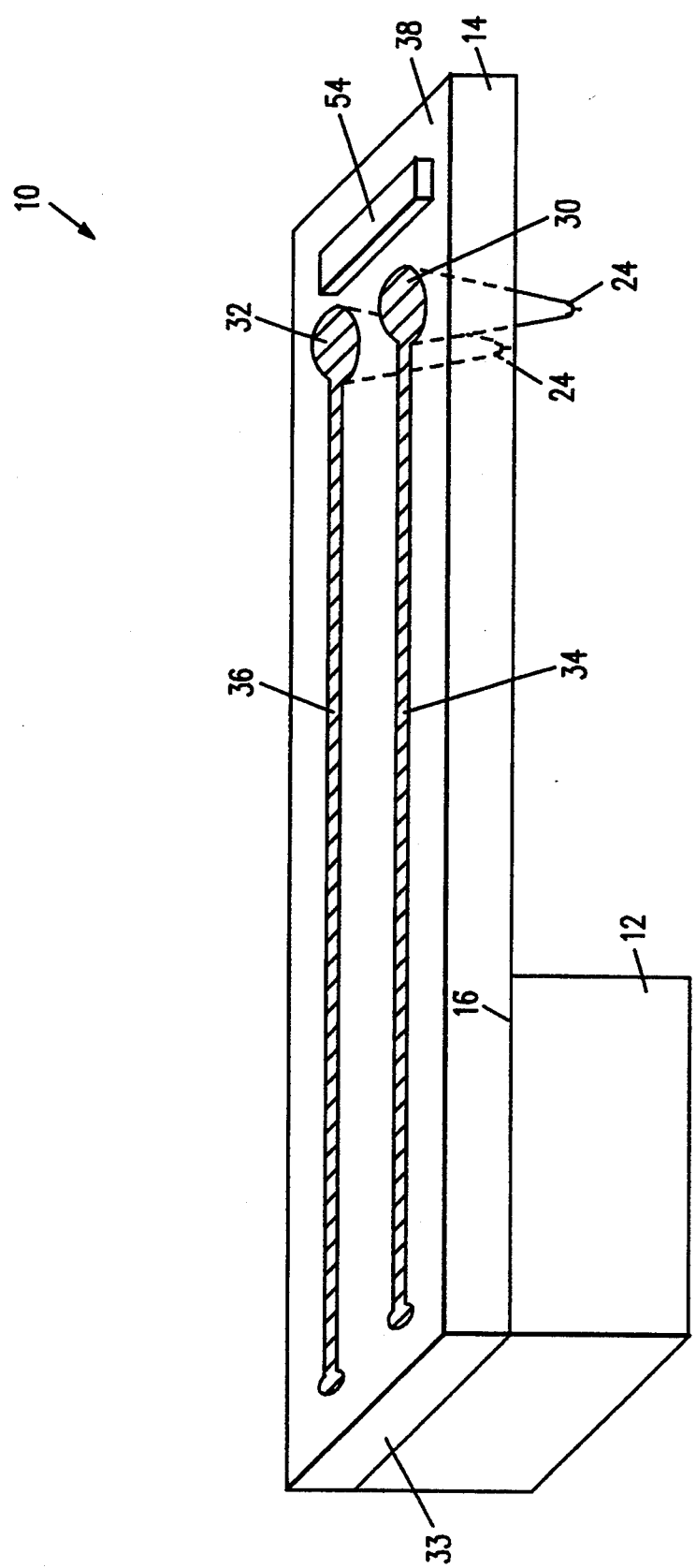
FIG. 10 is a top right-side perspective view illustrating only the mirror positioned on the top surface of the semiconductor probe.

As shown in FIG. 9, strain gage 40 is utilized in conjunction with mirror 54. Similarly, it should be clear to one skilled in the art that mirror 54 can be positioned at any location on support structure 14 that provides a sufficient deflection. Mirror 54 operates by redirecting a light beam (not shown in FIG. 9) which strikes the surface of mirror 54. The redirected light beam is detected by light sensors (not shown in FIG. 9) which indicate the amount of deflection by the movement of the light beam. Alternately, as shown in FIG. 10, the mirror can be utilized without strain gage 40.

Figure 11:
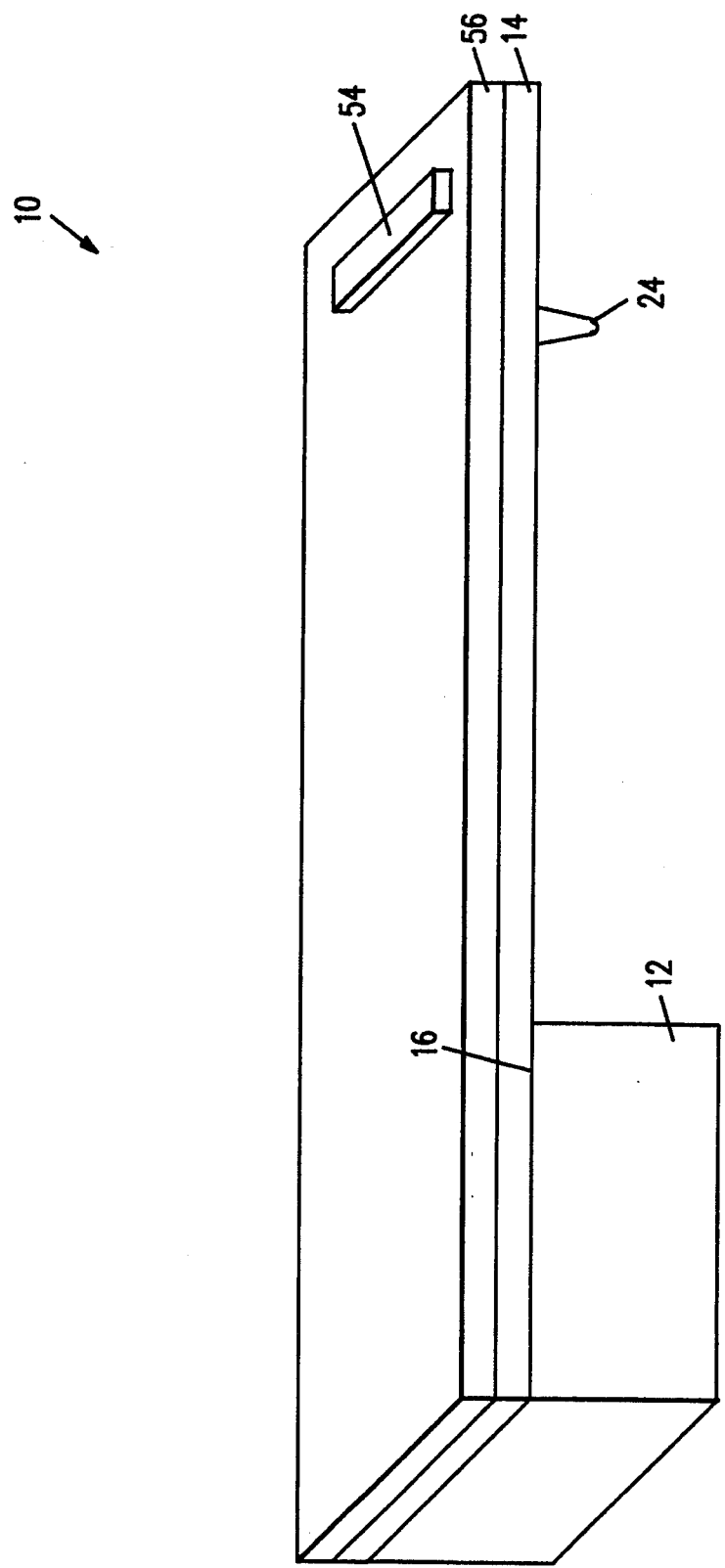
FIG. 11 is a top right-perspective view illustrating the insulative layer positioned on top of the support structure and the mirror positioned on top of the insulative layer.

As shown in FIG. 11, in a preferred embodiment of the present invention, insulating layer 56 is first formed on support structure 14 and then mirror 54 is formed on insulating layer 56. Insulation layer 56 electrically insulates each probe tip 30 and 32, input and output conductors 34 and 36, and strain input and output conductors 50 and 52. Insulating layer 56 additionally prevents surface contamination.

Figure 12:
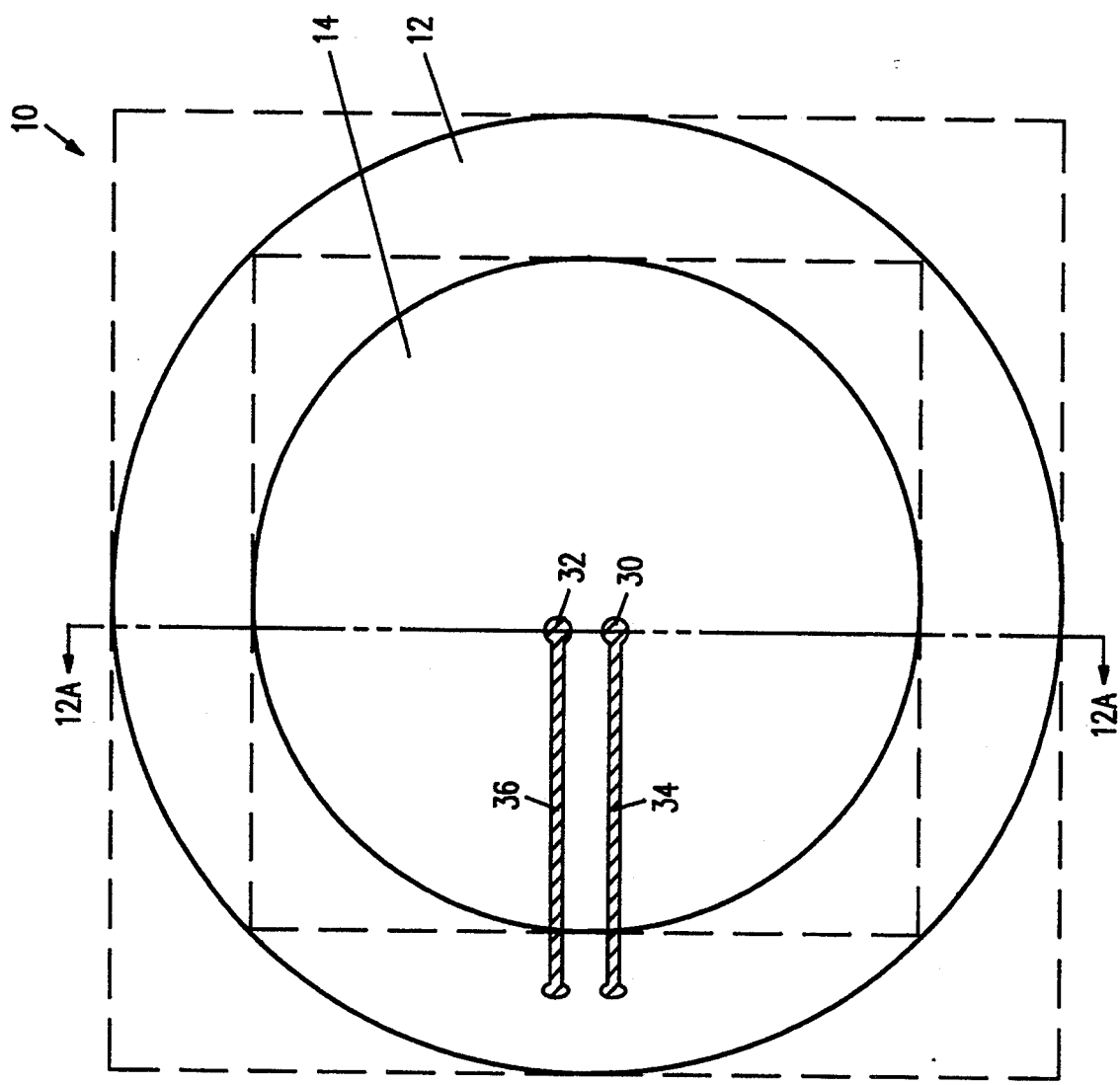
FIG. 12 is a plan view of the diaphragm embodiment illustrating a circular substrate in bold lines and a square substrate in dotted lines.
Figure 13:
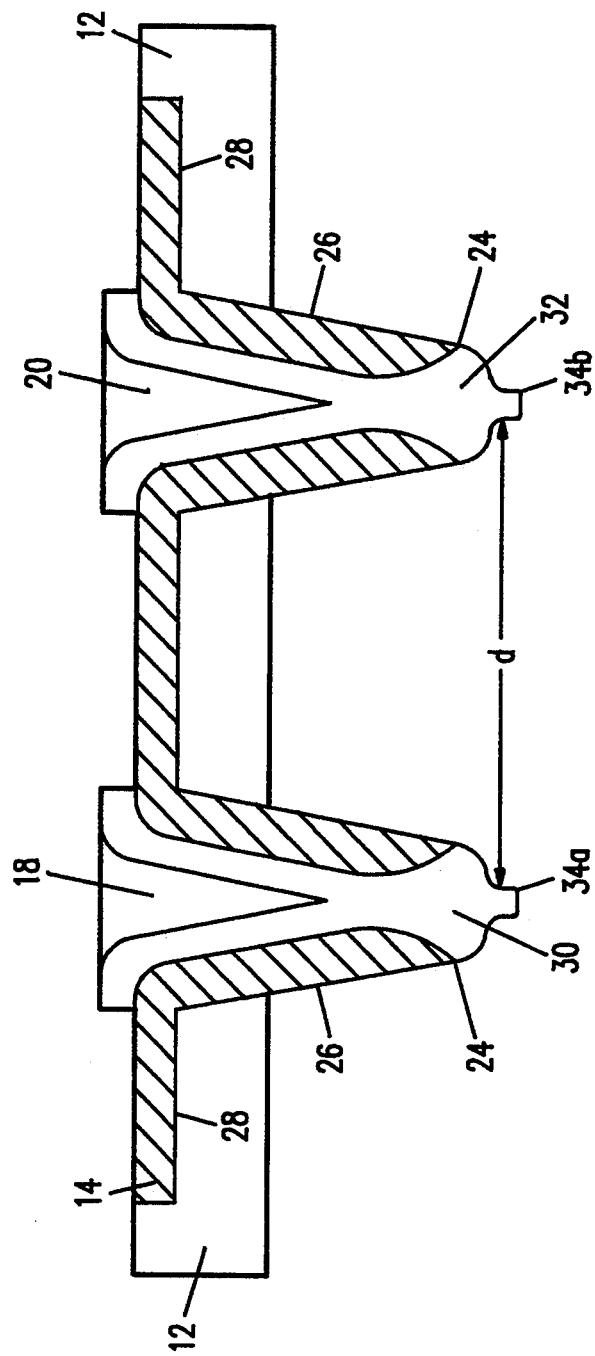
FIG. 13 is a cross-sectional view of the diaphragm embodiment along line 12A—12A of FIG. 12.
Figure 14:
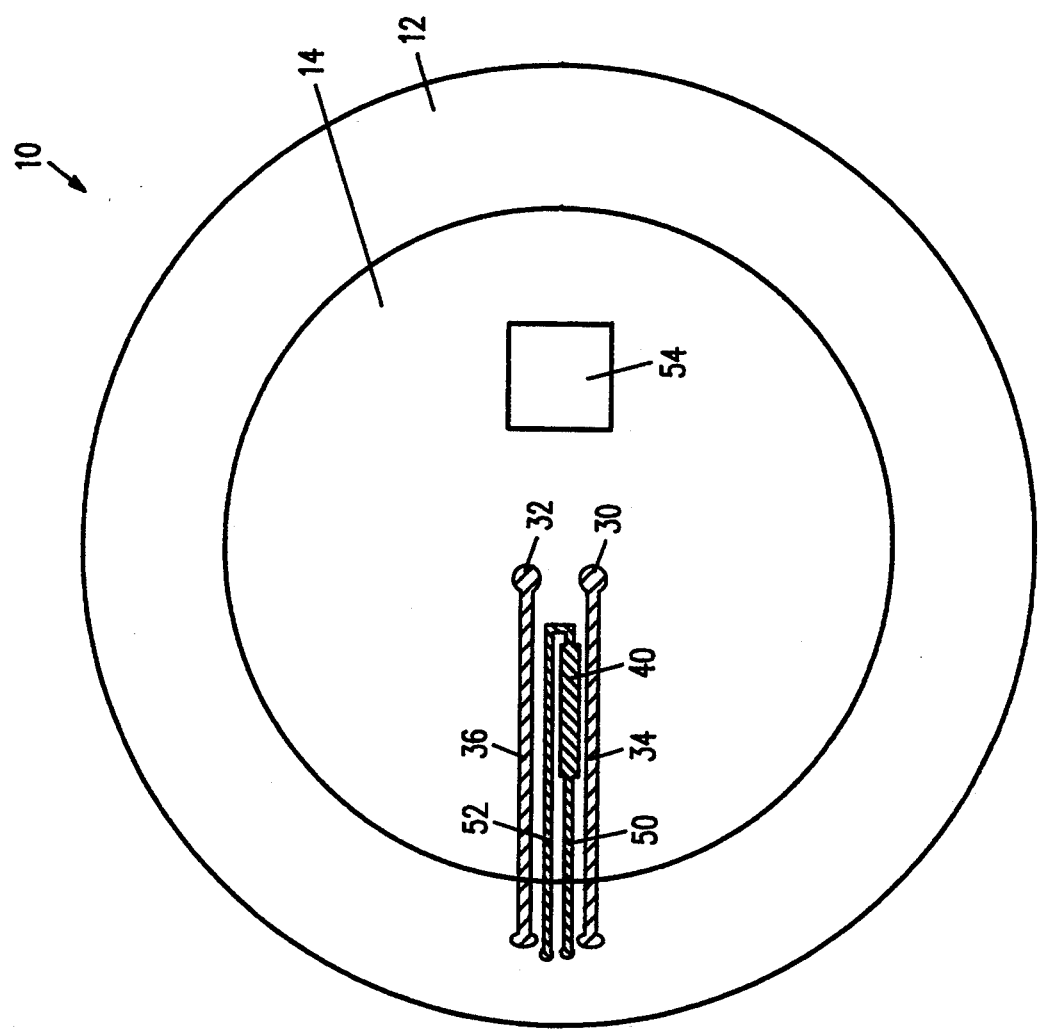
FIG. 14 is a plan view of the diaphragm embodiment illustrating the strain gage and the mirror positioned on top of the support structure.

In an alternative embodiment of the present invention, semiconductor probe 10 can be formed as a diaphragm. As shown in FIGS. 12, 13, and 14, substrate 12 surrounds support structure 14. The primary advantage of the diaphragm embodiment is that as the external positioning and control device initially physically contacts the surface of the semiconductor device, any additional lowering drives probe tips 30 and 32 in an essentially vertical direction.

This can be contrasted with the cantilever embodiment wherein as the external positioning and control device initially physically contacts the surface of the semiconductor device, any additional lowering drives probe tips 30 and 32 in a generally horizontal direction. By driving probe tips 30 and 32 in a generally horizontal direction, probe tips 30 and 32 scrape across the surface of the semiconductor device as probe tips 30 and 32 penetrate the layers of hydrocarbons and oxides. The vertical approach of the diaphragm embodiment, which provides a punch through effect, produces less wear on probe points 34a and 34b.

Figure 15:
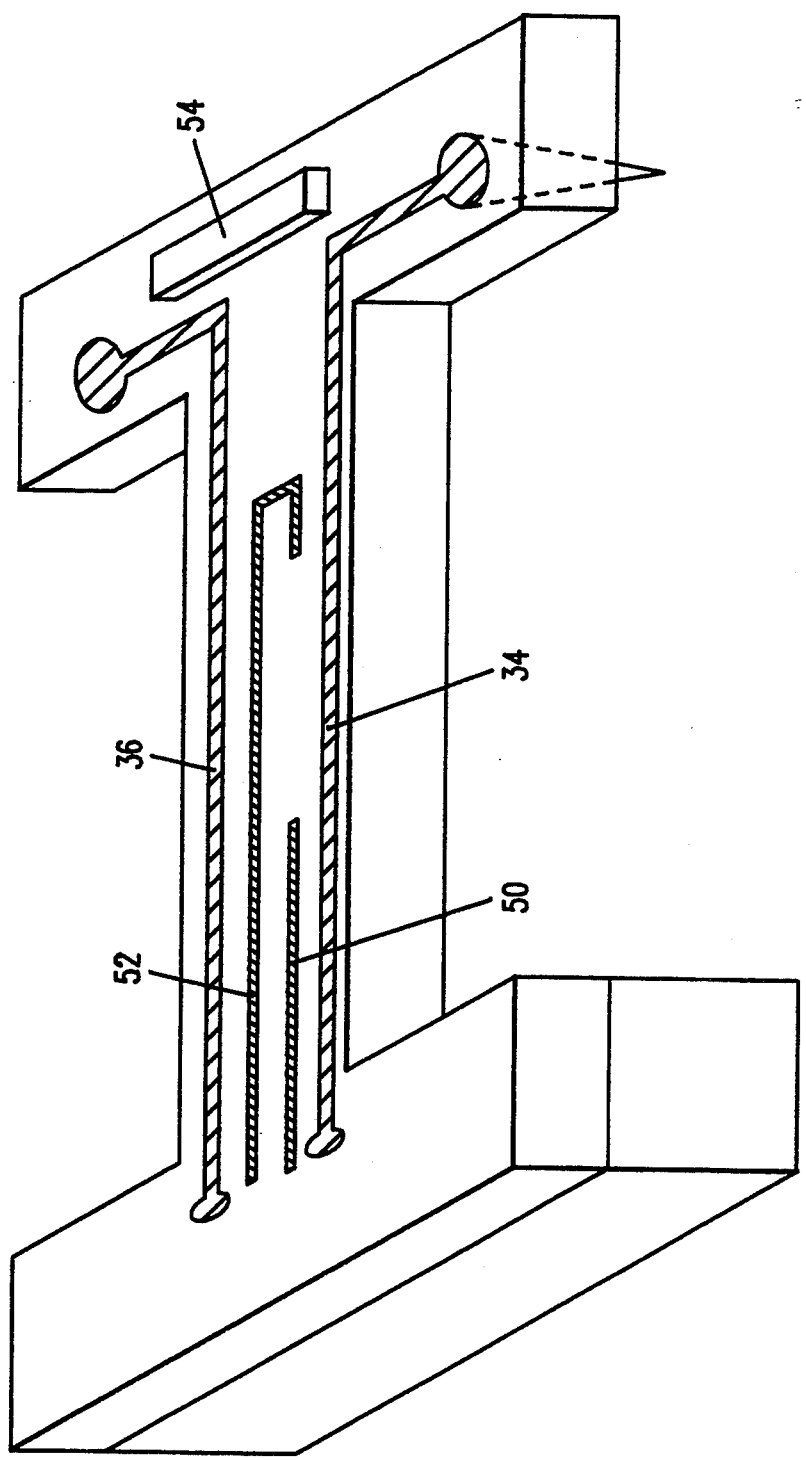
FIG. 15 is a top right-side view illustrating an alternative shape of the present invention.
Figure 16:
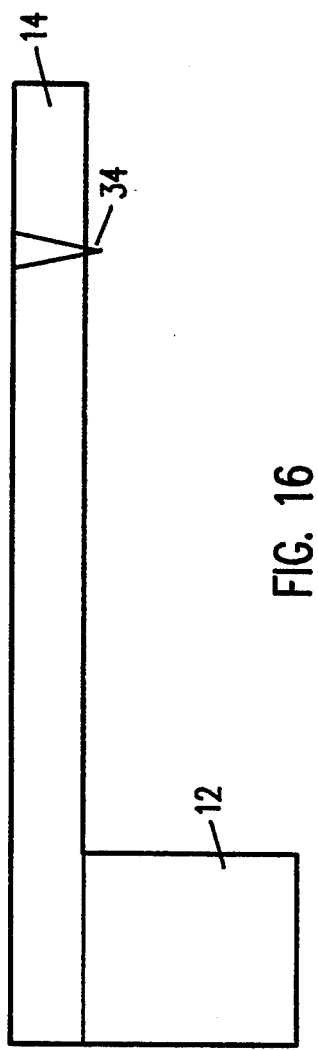
FIG. 16 is a right-side view illustrating the probe tips formed entirely within the support structure.

A number of alternative embodiments of the present invention are possible. First, multiple tips can be utilized so that multiple semiconductor devices can be probed at the same time. Second, as shown in FIG. 15 and as suggested by the second embodiment, semiconductor probe 10 can take on a variety of shapes. Third, as shown in FIG. 16, probe tips 30 and 32 can be formed entirely within support structure 14 with only probe points 34a and 34b extending beyond lower surface 28 of support structure 14.

Figure 17:
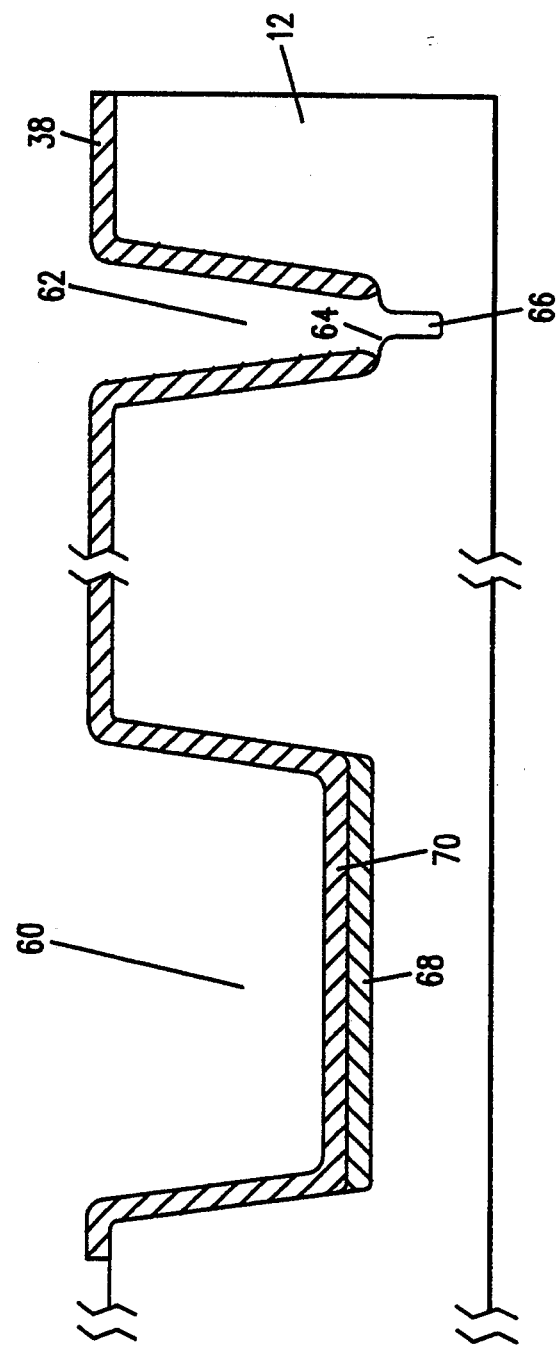
FIG. 17 is a right-side cross-sectional view illustrating the strain gage opening covered with a layer of nickel chromium and the strain gage opening and the probe tip opening covered with a layer of boron nitride.

Referring to FIG. 17, in a preferred embodiment, semiconductor probe 10 is fabricated by first forming strain gage opening 60 and probe tip opening 62 (only one of the two probe tip openings 18 and 20 is shown) in substrate 12. Strain gage opening 60 and probe tip opening 62 are formed by forming a photoresist pattern (not shown in FIG. 17), which defines strain gage opening 60 and probe tip opening 62, on the surface of semiconductor substrate 12. The photoresist pattern is formed by conventional photolithographic photoresist formation, exposure, development, and removal techniques. Substrate 12 is then isotropically etched with an etching chemistry comprising potassium hydroxide (KOH) or a similar chemistry.

Next, bottom side 64 of probe tip opening 62 is milled by focused ion beam micromachining to produce point opening 66 which is approximately three microns deep and three microns wide. Alternately, probe tip opening 62 and point opening 66 can be entirely formed by focused ion beam micromachining.

After strain gage opening 60 and probe tip opening 62 are formed, strain gage 40 is formed. Strain gage 40 is formed by depositing a layer of nickel chromium 68 or any piezoresistive material onto top surface 38 of semiconductor substrate 12. Hight resistivity materials are deposited to a uniform depth of approximately 0.5 microns while low resistivity materials are deposited to a uniform depth of approximately 1.0 microns. Next, a photoresist pattern (not shown in FIG. 17) which defines the strain gage, is formed on the surface of the substrate by conventional photolithographic photoresist formation, exposure, development, and removal techniques. The unmasked nickel chromium 68 is then etched with an etching chemistry comprising aquaregia or a similar chemistry until the unmasked nickel chromium 68 is removed from the surface of the substrate.

After strain gage 40 has been formed, support structure 14 is then formed. Support structure 14 is formed by depositing a layer of boron nitride 70 onto top surface 38 of substrate 12 and the layer of nickel chromium 68 to a uniform depth of in the range of 1.0 to 5.0 microns. In the preferred embodiment, a depth of 1.0 microns is utilized. As shown in FIG. 17, the layer of boron nitride 70 forms a film on top of the substrate and lines the sides of probe tip opening 62 but does not cover bottom side 64 of probe tip opening 62 or the point opening 66.

Figure 18:
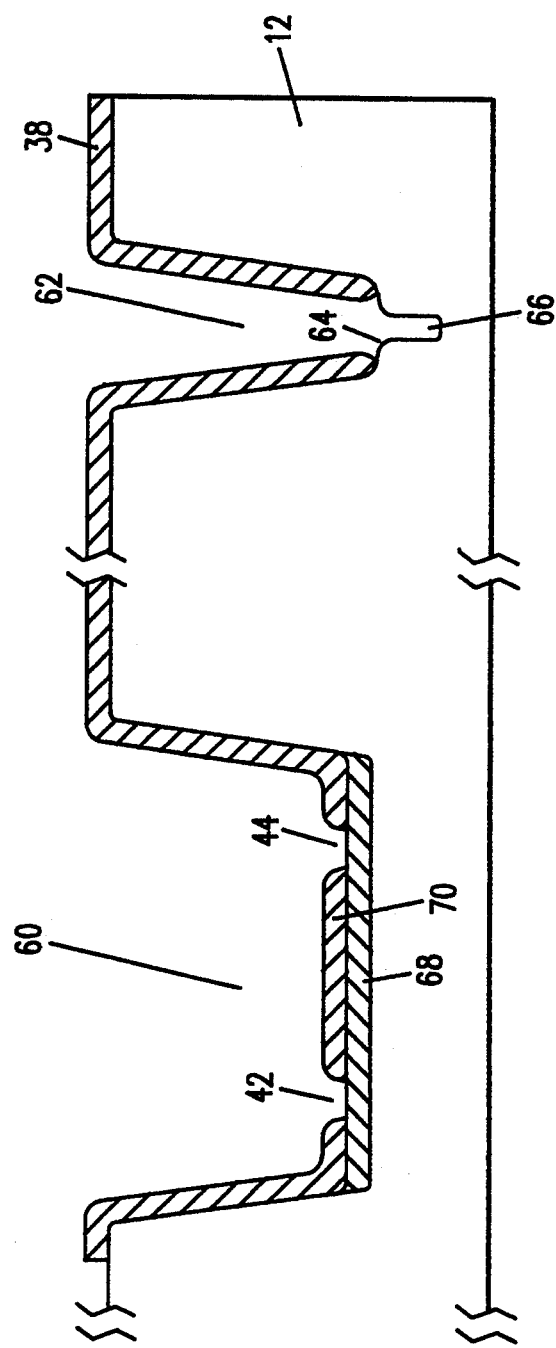
FIG. 18 is a right-side cross-sectional view illustrating FIG. 17 with strain input and output openings in the layer of boron nitride.

After support structure 14 has been formed, strain input opening 42 and strain output opening 44 are formed. As shown in FIG. 18, strain input and output openings 42 and 44, respectively, are formed by depositing a photoresist pattern (not shown in FIG. 18), which defines strain input opening 42 and strain output opening 44, on the surface of the layer of boron nitride 70 by conventional photolithographic photoresist formation, exposure, development, and removal techniques. The unmasked boron nitride 70 is then plasma etched with an etching chemistry comprising carbontetrafluoride and diatomic oxygen (CF4-O2) or a similar chemistry until the layer of nickel chromium 68 is exposed.

Figure 19:
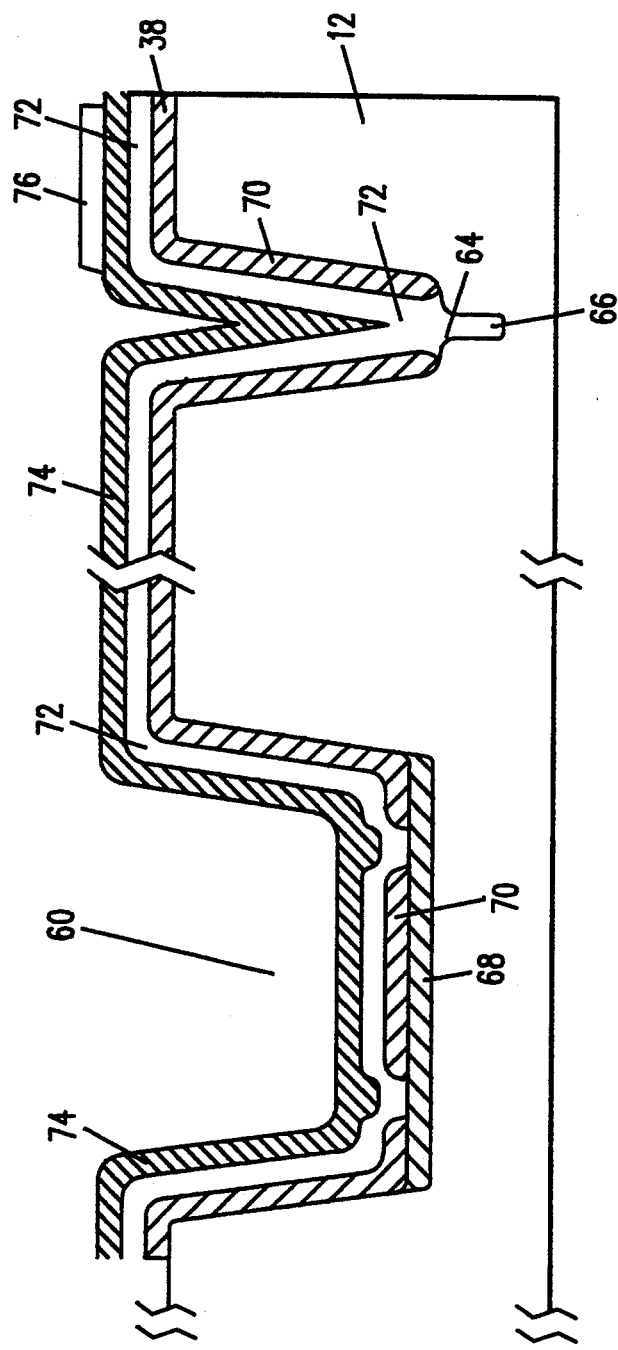
FIG. 19 is a right-side cross-sectional view illustrating FIG. 18 with a layer of metallic material, a layer of insulative material, and a layer of chromium, respectively.

After support structure 14 is formed, probe tips 30 and 32, input and output conductors 34 and 36, and strain input and output conductors 50 and 52, respectively, are formed. As shown in FIG. 19, probe tips 30 and 32, input and output conductors 34 and 36, and strain input and output conductors 50 and 52 are formed by depositing a layer of metallic material 72 on the layer of boron nitride 70 and within strain input opening 42, strain output opening 44, and probe tip opening 62 so that the layer of metallic material 72 covers bottom side 64 of probe tip opening 62 and fills point opening 66.

The layer of metallic material 72 can be deposited using any of a variety of semiconductor techniques like chemical vapor deposition, plasma enhanced chemical vapor deposition, low-pressure chemical vapor deposition (LPCVD), and ion chemical vapor deposition. The metalization layer 72 can include Os, W, Ti, Cr, Mo, Pt, Ir, Pd, Ag, Au, Cd, Ta, Re or combinations of the above. Other substances can also be used as dopants to obtain desired control of the metallurgy.

Next, a photoresist pattern (not shown in FIG. 19) which defines input and output conductors 34 and 36 and strain input and output conductors 50 and 52, respectively, is formed on the surface of the layer of metallic material 72 by conventional photolithographic photoresist formation, exposure, development, and removal techniques. The unmasked metallic material 72 is then etched with an etching chemistry comprising potasium hydroxide (KOH) or a similar chemistry until the unmasked metallic material 72 is removed from the layer of boron nitride 70. Input and output conductors 34 and 36 and strain input and output conductors 50 and 52, respectively, are connected to outside circuitry on the external positioning and control device by continuous integral metalization that is bonded using standard semiconductor bonding technology.

After probe tips 30 and 32, input and output conductors 34 and 36, and strain input and output conductors 50 and 52 are formed, insulative layer 56 and then mirror 54 are formed. Insulative layer 56 is formed by forming a layer of insulative material 74 on the layer of boron nitride 70, input and output conductors 34 and 36, and strain input and output conductors 50 and 52, respectively, to a uniform depth in the range of 0.25 to 0.5 microns. In the preferred embodiment, a depth of 0.5 microns is utilized. Next, a layer of chromium 76 or any other highly optically reflective material is formed on the layer of insulative material 74 to a uniform depth of approximately 500 Angstroms.

A photoresist pattern (not shown in FIG. 19) which defines mirror 54 is then formed on the surface of the layer of insulative material 74 by conventional photolithographic photoresist formation, exposure, development, and removal techniques. The unmasked chromium 76 is then etched with an etching chemistry comprising aquaregia or a similar chemistry until the unmasked chromium 76 is removed from the layer of insulative material 74.

Figure 20:
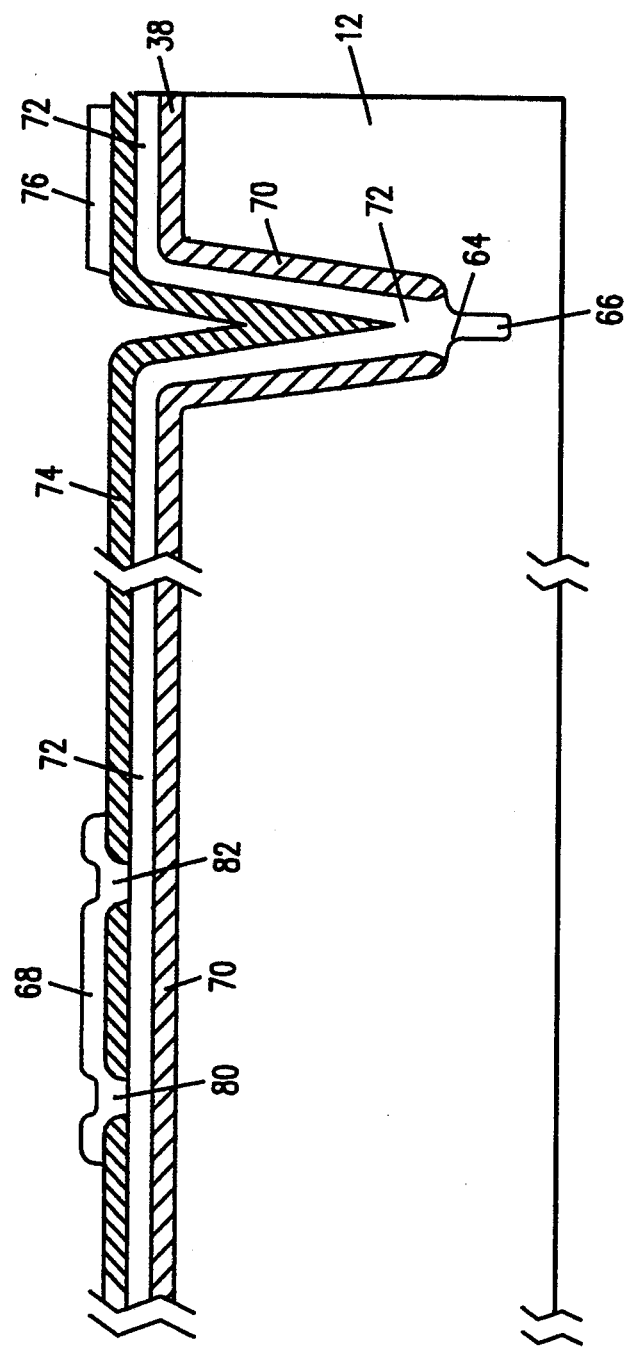
FIG. 20 is a right-side cross-sectional view illustrating the formation of the strain gage on the top surface of the semiconductor probe.

Alternatively, as stated above, strain gage 40 can be formed on top surface 38 of support structure 14. Referring to FIG. 20, which shows the above-described sequence of events except the formation of strain gage 40, when strain gage 40 is formed on top surface 38, strain gage input opening 80 and strain gage output opening 82 are formed in the layer of insulative material 74. Strain gage input and output openings 80 and 82 are formed by forming a photoresist pattern (not shown in FIG. 20), which defines strain gage input and output openings 80 and 82, respectively, on the surface of the layer of insulative material 74 by conventional photolithographic photoresist formation, exposure, development, and removal techniques. The unmasked insulative material 74 is then plasma etched with an etching chemistry comprising carbontetraflouride and diatomic oxygen (CF4-O2) or a similar chemistry until the layer of metallic material 72 is exposed.

Next, a layer of nickel chromium 68 is deposited on the layer of insulative material 74, filling up strain gage input and output openings 80 and 82, respectively. Following this, a photoresist pattern (not shown in FIG. 20) which defines strain gage 40 is then formed on the surface of the layer of nickel chromium 68 by conventional photolithographic photoresist formation, exposure, development, and removal techniques. The unmasked nickel chromium 68 is then etched with an etching chemistry comprising aquaregia or a similar chemistry until the unmasked chromium 68 is removed from the layer of insulating material 74.

Once mirror 54 has been formed, substrate 12 is partially removed to form the cantilever. Substrate 12 is removed by first turning the semiconductor probe 10 over. Next, a photoresist pattern (not shown) which defines the remaining substrate 12 is then formed on the surface of substrate 12 by conventional photolithographic photoresist formation, exposure, development, and removal techniques. The substrate is then etched with an etching chemistry comprising potasium hydroxide (KOH) or a similar chemistry until layer of the layer of boron nitride 70 is exposed. Following this, the probe points can be milled to form a sharp point, a ball point, or a cylindrical point.

As stated above, when the layer of boron nitride 70 is deposited, the boron nitride 70 does not cover the bottom side of the probe tip opening. Alternatively, the present invention can be fabricated by covering the bottom side with the layer of boron nitride 70 and then, following the above substrate etching step, mill the probe point to remove the boron nitride 70 from the probe points. The probe points can be milled to produce a probe point that has a sharp point, a ball point, or a cylindrical point.

It should be understood that various alternatives to the structures described herein may be employed in practicing the present invention. It is intended that the following claims define the invention and that the structure within the scope of these claims and their equivalents be covered thereby.

What is claimed is:

1. A semiconductor scanning resistance probe responsive to an external positioning and control device for generating a resistivity current in a semiconductor device, the semiconductor scanning resistance probe comprising:
   a semiconductor substrate;
   a cantilever formed on the semiconductor substrate, the cantilever having a plurality of projections and a corresponding plurality of probe tip openings, each projection having a distal end, each probe tip opening extending through the cantilever to the distal end of one projection; and
   a plurality of probes, each probe being formed within a corresponding one of the probe tip openings so that a portion of each probe extends beyond the distal end of said one projection,
   whereby the resistivity current flows between the probes when the plurality of probes are placed into contact with the semiconductor device by the external positioning and control device.

2. The semiconductor scanning resistance probe of claim 1 wherein the plurality of probe tip openings are located adjacent to the distal end of the cantilever.

3. The semiconductor scanning resistance probe of claim 1 and further comprising a strain gage formed on the cantilever at an intermediate position located between the proximate end and the distal end of the cantilever.

4. The semiconductor scanning resistance probe of claim 3 and further comprising:
   a plurality of probe conductive strips formed on the cantilever, each probe conductive strip contacting one probe;
   a layer of insulation material formed on the the cantilever, the plurality of probe conductive strips, and the plurality of probes.

5. The semiconductor scanning resistance probe of claim 4 wherein the layer of insulation material is further formed on the strain gage.

6. The semiconductor scanning resistance probe of claim 5 and further comprising a mirror formed on the layer of insulation material.

7. The semiconductor scanning resistance probe of claim 3 wherein the cantilever further comprises a strain gage opening formed therethrough at the intermediate position.

8. The semiconductor scanning resistance probe of claim 7 wherein the scanning resistance probe further comprises a pair of strain gage conductors formed on the cantilever and in the strain gage opening, the pair of strain gage conductors contacting the strain gage.

9. The semiconductor scanning resistance probe of claim 8 wherein the strain gage comprises a piezoelectric material.

10. The semiconductor scanning resistance probe of claim 1 and further comprising a mirror formed on the cantilever.

11. A semiconductor scanning resistance probe responsive to an external positioning and control device for generating a resistivity current in a semiconductor device, the semiconductor scanning resistance probe comprising:
    a semiconductor substrate;
    a cantilever formed on the semiconductor substrate, the cantilever having a plurality of probe tip openings formed therethrough; and
    a plurality of probes, each probe being formed within a corresponding one of the probe tip openings so that a portion of each probe extends beyond the cantilever,
    whereby the resistivity current flows between probes when the plurality of probes are placed into contact with the semiconductor device by the external positioning and control device.

12. A semiconductor scanning resistance probe responsive to an external positioning and control device for generating a resistivity current in a semiconductor device, the semiconductor scanning resistance probe comprising:
    a semiconductor substrate having a stepped inner surface and a plurality of first openings formed therethrough;
    a support structure formed on the stepped inner surface, the support structure having a plurality of projections and a corresponding plurality of probe tip openings, each projection extending through one of the first openings and having a distal end, each probe tip opening extending through the support structure to the distal end of one projection; and
    a plurality of probes, each probe being formed within a corresponding one of the probe tip openings so that a portion of each probe extends beyond the distal end of said one projection,
    whereby the resistivity current flows between probes when the plurality of probes are placed into contact with the semiconductor device by the external positioning and control device.

13. The semiconductor scanning resistance probe of claim 12 and further comprising a strain gage formed on the support structure at an intermediate position located between opposite sides of the support structure.

14. The semiconductor scanning resistance probe of claim 13 and further comprising:
    a plurality of probe conductive strips formed on the support structure, each probe conductive strip contacting one probe;
    a layer of insulation material formed on the support structure, the plurality of probe conductive strips, and the plurality of probes.

15. The semiconductor scanning resistance probe of claim 14 wherein the layer of insulation material is further formed on the strain gage.

16. The semiconductor scanning resistance probe of claim 15 and further comprising a mirror formed on the layer of insulation material.

17. The semiconductor scanning resistance probe of claim 16 wherein the support structure further comprises a strain gage opening formed therethrough at the intermediate position,
    wherein the semiconductor scanning resistance probe further comprises a pair of strain gage conductors formed on the support structure and in the strain gage opening to contact the strain gage.

18. The semiconductor scanning resistance probe of claim 17 wherein the strain gage comprises a piezoelectric material.

19. The semiconductor scanning resistance probe of claim 12 and further comprising a mirror formed on the support structure.

20. A method of fabricating a semiconductor scanning resistance probe comprising the steps of:
    providing a semiconductor substrate having a top surface;
    forming a support structure having a plurality of probe tip openings, an outer surface, a proximate end, and a distal end and being formed on the top surface of the semiconductor substrate to produce a cantilever, each probe tip opening extending through the support structure from a trace end to a cone end, the outer surface being cone-shaped on one side of each probe tip opening so that an apex of the cone-shaped outer surface forms the cone end; and
    forming a plurality of probe tip means for conducting a probe current in response to the resistivity of the semiconductor device, each probe tip means corresponding to one of the plurality of probe tip openings and being formed within the corresponding one probe tip opening and on the outer surface of the support structure from the corresponding one probe tip opening to the proximate end, the probe tip means extending beyond the cone end of the support structure.

21. A method of fabricating a semiconductor scanning resistance probe comprising the steps of:
   providing a semiconductor substrate;
   forming a plurality of probe tip openings in the semiconductor substrate, each probe tip opening having a side wall and a bottom side;
   forming a layer of support material on the semiconductor substrate, the layer of support material covering the sidewalls of each probe tip opening while leaving the bottom side of each probe tip opening uncovered, the layer of support material having a proximate end and a distal end;
   forming a layer of first conductive material on the support material and the substrate at the bottom side of each probe tip opening, the first conductive material covering the bottom side of each probe tip opening forming a probe tip;
   etching the layer of first conductive material to form a plurality of probe tip conductors; and
   etching the substrate to form a cantilever.

22. The method of claim 21 wherein each probe tip conductor connects the first conductive material formed in one probe tip opening to the proximate end of the layer of support material.

23. The method of claim 22 and further comprising the steps of:
   forming a strain gage opening in the semiconductor substrate;
   forming a layer of second conductive material within the strain gage opening to form a strain gage, the strain gage having an input end and a output end;
   forming a plurality of strain gage openings in the layer of support material, the plurality of strain gage openings exposing the input end and the output end of the strain gage; and
   wherein the layer of first conductive material is further etched to form an input trace and an output trace, the input trace forming an electrical contact with the input end of the strain gage and extending from the input end to the proximate end and the output trace forming an electrical contact with the output end of the strain gage and extending from the output end to the proximate end.

24. The method of claim 23 and further comprising the step of forming a layer of insulation material on the layer of support material, each probe tip trace, the input trace, and the output trace.

25. The method of claim 24 and further comprising the steps of:
   forming a layer of reflective material on the layer of insulation material; and
   etching the layer of reflective material to form a mirror.

26. The method of claim 24 wherein the layer of first conductive material is further etched to form a strain gage, the strain gage extending from the proximate end to an intermediate point between the proximate end and the distal end.

27. The method of claim 21 further comprising the steps of:
   forming a layer of reflective material on the layer of support material; and
   etching the layer of reflective material to form a mirror.

28. A method of fabricating a semiconductor scanning resistance probe comprising the steps of:
   providing a semiconductor substrate;
   forming a plurality of probe tip openings in the semiconductor substrate, each probe tip opening having a side wall and a bottom side;
   forming a layer of support material on the semiconductor substrate, the layer of support material covering the sidewalls and the bottom side of each probe tip opening, the layer of support material having a proximate end and a distal end;
   forming a layer of first conductive material on the support material;
   etching the layer of first conductive material to form a plurality of probe tip conductors;
   etching the substrate to form a cantilever; and
   milling the layer of support material and the layer of first conductive material to form a probe tip.

29. The method of claim 28 wherein each probe tip conductor connects the first conductive material formed in one probe tip opening to the proximate end of the layer of support material.

30. A method of fabricating a semiconductor scanning resistance probe comprising the steps of:
   providing a semiconductor substrate;
   forming a plurality of probe tip openings in the semiconductor substrate, each probe tip opening having a side wall and a bottom side;
   forming a layer of support material on the semiconductor substrate, the layer of support material covering the sidewalls of each probe tip opening while leaving the bottom side of each probe tip opening uncovered, the layer of support material having a side;
   forming a layer of first conductive material on the support material and the substrate at the bottom side of each probe tip opening, the first conductive material covering the bottom side of each probe tip opening forming a probe tip;
   etching the layer of first conductive material to form a plurality of probe tip conductors; and
   etching the substrate to form a diaphragm.

31. The method of claim 30 wherein each probe tip conductor connects the first conductive material formed in one probe tip opening to the side of the layer of support material.

32. A method of fabricating a semiconductor scanning resistance probe comprising the steps of:
   providing a semiconductor substrate;
   forming a plurality of probe tip openings in the semiconductor substrate, each probe tip opening having a side wall and a bottom side;
   forming a layer of support material on the semiconductor substrate, the layer of support material covering the sidewalls and the bottom side of each probe tip opening, the layer of support material having a side;
   forming a layer of first conductive material on the support material;
   etching the layer of first conductive material to form a plurality of probe tip conductors;
   etching the substrate to form a diaphragm; and
   milling the layer of support material and the layer of first conductive material to form a probe tip.

33. The method of claim 32 wherein each probe tip conductor connects the first conductive material formed in one probe tip opening to a side of the support material.

* * * * *